United States Patent [19]

Pitt

[11] 4,051,182

[45] Sept. 27, 1977

[54] PROCESS FOR THE MANUFACTURE OF α-CHLOROPROPIONYL CHLORIDE

[75] Inventor: Harold M. Pitt, Lafayette, Calif.

[73] Assignee: Stauffer Chemical Company, Westport, Conn.

[21] Appl. No.: 676,022

[22] Filed: Apr. 12, 1976

[51] Int. Cl.² .............................................. C07C 51/58
[52] U.S. Cl. ........................... 260/544 Y; 260/654 D; 260/658 R
[58] Field of Search ............ 260/544 Y, 654 D, 658 R

[56] References Cited

U.S. PATENT DOCUMENTS

| | | | |
|---|---|---|---|
| 1,304,108 | 5/1919 | Simon et al. | 260/544 Y |
| 1,976,265 | 10/1934 | Mugdan et al. | 260/544 Y |
| 2,111,509 | 3/1938 | Loder | 260/544 Y |
| 2,778,851 | 1/1957 | Kundiger et al. | 260/544 Y |
| 3,509,210 | 4/1970 | Gaertner et al. | 260/544 Y |
| 3,674,664 | 7/1972 | Larsen et al. | 260/544 Y |
| 3,880,923 | 4/1975 | Scheidmeir et al. | 260/544 Y |
| 3,959,367 | 5/1976 | Jeffrey | 260/544 Y |

*Primary Examiner*—Norman Morgenstern
*Attorney, Agent, or Firm*—M. Henry Heines; Michael J. Bradley

[57] ABSTRACT

A process of manufacture is disclosed herein, whereby α-chloropropionyl chloride, a compound which is useful as an intermediate in the production of N,N-diethyl 2(α-naphthoxy) propionamide, a useful herbicide, is produced by the chlorination of 1,2-dichloropropane to form 1,1,2-trichloropropane, which is cracked to form 1,1-dichloropropene-1, which is subsequently oxidized to produce the desired product, α-chloropropionyl chloride.

24 Claims, No Drawings

PROCESS FOR THE MANUFACTURE OF α-CHLOROPROPIONYL CHLORIDE

BACKGROUND OF THE INVENTION

As disclosed in U.S. Pat. No. 3,408,671, the compound N,N-diethyl 2(α-naphthoxy)propionamide has been found to be a useful herbicide. The above patent describes a method of preparation of this herbicide wherein α-naphthol is reacted with N,N-diethyl-α-bromopropionamide in the presence of a 25% solution of sodium methoxide in methanol.

An alternative route for the manufacture of the above herbicide is described in co-pending application Ser. No. 604,968. Pursuant to the latter, diethylamine is reacted with an α-halopropionic acid in the presence of phosphoryl chloride, to produce an N,N-diethyl-α-halopropionamide, which is in turn reacted with α-naphthol in the presence of an alkali metal hydroxide, to form the desired product. An undesirable aspect of this process is the production of phosphoric acid wastes and the problem of their disposal.

A third alternative utilizes the same intermediate, N,N-diethyl-α-chloropropionamide, but arrives at this intermediate by reacting diethylamine with α-chloropropionyl chloride in the presence of an excess of an aqueous solution of an alkali metal hydroxide. The production of phosphoric acid wastes is avoided. This type of reaction is disclosed in U.S. Pat. No. 3,914,302.

The compound α-chloropropionyl chloride is a known compound which can be manufactured by a variety of techniques, examples of which are as follows: reaction of α-chloropropionic acid with phosgene in the presence of dimethyl formamide catalyst; the reaction of α-chloropropionic acid with thionyl chloride [Leimu, *Ber.* 70, 1049 (1937)]; the reaction of propionic acid with $SO_2Cl_2$ and $I_2$, or with $SO_2Cl_2$ and benzoyl peroxide in carbon tetrachloride [Kharasch et al., *J. Am. Chem. Soc.* 62, 927–928 (1940)]; the reaction of propionyl chloride with chlorine and iodine [Wolfenstein et al., *Ber.* 41, 735 (1908); Michael, *Ber.* 34, 4035, 4037 (1901)]; and the reaction of $(CH_3CHOHCO_2)_2Ca$ with PCl [Wurtz, *Ann.* 107, 194 (1858)].

Starting materials for the above reactions are either expensive or obtainable through a series of additional reactions which are costly to run and provide less than stoichiometric yield. The object of the present invention is to provide a process for the manufacture of α-chloropropionyl chloride from an alternate starting material, 1,2-dichloropropane, in a three-step process. Use of 1,2-dichloropropane as a starting material will be advantageous when this compound can be obtained more cheaply than other starting materials. Its use will be further advantageous in commercial plants where by-products of the chlorination of this compound (the first step of the process of the present invention as described more fully hereinbelow) can be used as feed for the manufacture of perchloroethylene and carbon tetrachloride.

Another object of the present invention is to provide a process for the manufacture of α-chloropropionyl chloride from 1,1-dichloropropene-1 in a one-step process.

SUMMARY OF THE INVENTION

In one aspect, this invention comprises a process for the production of α-chloropropionyl chloride comprising:

a. reacting 1,2-dichloropropane with chlorine gas to produce, 1,1,2-trichloropropane, b. reacting the product of step (a) with sodium hydroxide to form 1,1-dichloropropene-1, and c. reacting the product of step (b) with oxygen in a photochemical chlorine- or bromine-sensitized oxidation to produce the desired product.

In another aspect, the invention herein comprises a process for the production of α-chloropropionyl chloride comprising the photochemical chlorine- or bromine-sensitized oxidation of 1,1-dichloropropene-1 to produce the desired product.

DETAILED DESCRIPTION OF THE INVENTION

Step (a)

In the practice of the invention, liquid 1,2-dichloropropane is reacted with an approximately stoichiometric amount of gaseous chlorine in the presence of a suitable chlorination catalyst or catalysts or produce 1,1,2-trichloropropane and HCl. Examples of suitable chlorination catalysts are ferric chloride, aluminum chloride, iodine, sulfur, iron, and iron with ultraviolet light. Perferably, catalytic amounts of iodine and anhydrous aluminum chloride are used, and more preferably, at concentrations ranging from about 0.5 to about 4% by weight each with respect to 1,2-dichloropropane. The reaction is conducted at approximately atmospheric pressure and at a temperature of between about 25° C and about 90° C, preferably between about 25° C and about 60° C.

Step (b)

The 1,1,2-trichloropropane is then reacted with a basic material to produce 1,1-dichloropropene-1. Any basic material can be used. Examples of such bases in the liquid phase reaction are aqueous or alcohol solutions of sodium and/or potassium hydroxide, alkaline earth metal hydroxide, and sodium carbonate. The process can also be carried out in the gas phase, over a catalyst comprising any hydrogen chloride-removing catalyst, for example barium chloride on charcoal. Preferably, the reaction is run in the liquid phase using sodium hydroxide as the cracking agent. Most preferably, the reaction is run in the presence of a catalytic amount of a phase transfer catalyst, i.e., any catalyst which facilitates the transfer of a chemical species from one liquid phase to another. Examples of such catalysts are Aliquot 336® (Armour Chemical Co.) and benzyltrimethylammonium chloride or bromide. When a phase transfer catalyst is not used, an excess of sodium hydroxide will be required for the reaction to proceed at a reasonable rate. In such case, the amount of excess ranges from about 25 to about 100%. The reaction takes place at approximately atmospheric pressure and the reaction mixture forms a liquid medium consisting of two liquid phases which are subsequently separated, the desired product residing in the upper phase. The reaction proceeds at a temperature ranging from about 60° C to about 110° C, preferably from about 70° C to about 80° C.

Step (c)

In the final step of the reaction, 1,1-dichloropropene-1 is reacted with an oxygen-containing gas in the liquid phase in the presence of a catalytic amount of free chlorine or bromine and a means for activating the halogen, while continuously contacting the reaction mixture with an amide catalyst selected from the group of primary and secondary amides of the lower alkyls, to form the desired product.

In the absence of the amide catalyst, the product of the halogen-sensitized oxidation is a mixture of α-chloropropionyl chloride and 2,2-dichloro-3-methyloxirane (hereinafter referred to a gem-dichloropropylene oxide). The function of the amide catalyst is to catalyze the continuous rearrangement of the gem-dichloropropylene oxide as soon as it is formed to α-chloropropionyl chloride, the desired product.

As stated above, the amide catalyst can be selected from primary and secondary amides of the lower alkyls. By lower alkyls is meant those alkyls having from 1 to 6 carbon atoms. Preferably, dialkylformamide is used as the catalyst but most preferably, dimethylformamide is employed as the catalyst for this rearrangement reaction in a catalytically effective amount. The amount of catalyst employed can range from about 0.001 to about 1.0 volume percent of 1,1-dichloropropene-1 in the reaction mixture and preferably from about 0.01 to about 0.1 volume percent of the amide based on 1,1-dichloropropene-1.

The amide catalyst can be added in several aliquot portions at the beginning and distributed throughout the period of the liquid phase oxidative reaction of 1,1-dichloropropene-1 to α-chloropropionyl chloride and gem-dichloropropylene oxide. Alternatively, the amide catalyst can be added continuously to the reaction mass during a batch operation, or with the 1,1-dichloropropene-1 feed to a continuous operation. By addition of the amide catalyst at the beginning of the reaction and continuously or periodically adding additional amounts of catalysts as the catalyst is consumed, a build-up of gem-dichloropropylene oxide in the system is avoided and the reaction proceeds smoothly and is easily controlled in terms of temperature and reaction rate as colored by-products which absorb the light rays and inhibit the reaction are continuously oxidized to non-colored by-products.

The catalytic amount of free chlorine or bromine can be from about 0.1 to about 3.84 mole %, preferably from about 0.8 to about 3.84 mole % of the oxygen added without causing further chlorination of the 1,1-dichloropropene-1.

The reaction can be conducted at temperatures ranging from about 24° C to about 100° C, preferably from about 60° C to about 90° C, and most preferably from about 65° C to about 80° C.

The oxygen is preferably added in the form of O$_2$, but could alternatively be added in the form of air. The halogen preferred for the reaction is chlorine and the preferred halogen activating source is ultraviolet light. The ultraviolet wavelength range preferred for this reaction is that sufficient to cause the disassociation of chlorine to create a free radical. Normally this wavelength range is within the chlorine absorption band and sufficient to activate the chlorine molecule.

In order to illustrate the merits of the present invention, the following example is provided.

EXAMPLE

In a 2 liter reactor were placed 1 liter of 1,2-dichloropropane, 5 g of iodine, and 25 g of anhydrous aluminum chloride. Chlorine gas was bubbled through the reactor while the temperature was held within 30–35 C by water and ice cooling. At the completion of the reaction, the product was washed with sodium bisulfate solution. The resulting two-phase mixture was separated and the organic phase containing the product was distilled. After removing a low-boiling fraction (60–70° C), the remainder was taken overhead on a rotary evaporator to yield 1306 g (93% yield) of product with 36 g of tar remaining in the pot.

Into a 250 ml Erlenmeyer flask equipped with a magnetic stirrer and a condenser, were placed 74 g of 1,1,2-trichloropropane, 30 ml of 50% NaCH, 40 ml water, and 0.5 g of benzyltrimethylammonium bromide. Heat was applied from the hot plate to start the reaction after which a low heat setting was maintained. At the completion of the reaction, additional water was added to dissolve the salt. A yield of 99.5% was achieved, with the product 1,1-dichloropropene-1 forming the upper layer of a two-phase liquid system. The phases were subsequently separated.

A reactor with a gas inlet on the bottom was charged with 500 cc (585 g) of 1,1-dichloropropene-1 and 0.13 cc of dimethylformamide, to give a liquid height of about 12 inches. Oxygen and chlorine were bubbled into the solution at approximately 600 cc/min and 75 cc/min, respectively. The liquid was illuminated by F15T8 Bl fluorescent lights. Emissions of these 15 watt lights peaks at approximately 3000 A. After the first hour of the reaction, an additional 0.3 cc of dimethylformamide was added to the reaction mixture. A further 0.2 cc was added after the second hour, and a final 0.3 cc was added after the third hour. At the end of 3 hours and 50 minutes, 610 g of solution remained in the reaction vessel. Approximately 50 g of alkene has been lost to the excess gas which was bubbled through the solution. On a weight basis the solution consisted of 3.38% alkene, 84.12% α-chloropropionyl chloride, no oxides, and 12.31% high boilers. The solution was then distilled to yield 500 g of α-chloropropionyl chloride (74.7% yield).

What is claimed is:

1. A process for the manufacture of α-chloropropionyl chloride comprising the steps of
   a. reacting 1,2-dichloropropane in the liquid phase at a temperature in the range of from about 25° C to 90° C with gaseous chlorine in the presence of a catalyst selected from the group consisting of ferric chloride, aluminum chloride, iodine, sulfur, iron, iron in the presence of ultraviolet light and mixtures thereof, to form 1,1,2-trichloropropane, and separating the product 1,1,2-trichloropropane;
   b. reacting the 1,1,2-trichloropropane of step (a) with a base selected from aqueous or alcohol solutions of sodium and/or potassium hydroxides, alkaline earth metal hydroxides and sodium carbonate in the liquid phase or in the gaseous phase in the presence of a hydrogen chloride removing catalyst at a temperature in the range of from about 60° C to 110° C, and separating the product 1,1-dichloropropene-1; and
   c. reacting the 1,1-dichloropropene-1 of step (b) in the liquid phase at a temperature in the range of from about 24° C to about 100° C with oxygen in the presence of chlorine or bromine and an activating agent for the chlorine or bromine and further in the presence of a lower alkyl-primary- or -secondary-amide and recovering the produced α-chloropropionyl chloride.

2. The process of claim 1 wherein the reaction of step (a) is conducted in the presence of catalytic amounts of iodine and anhydrous aluminum chloride.

3. The process of claim 1 wherein the reaction of step (a) is conducted in the presence of iodine and anhydrous aluminum chloride at concentrations between about 0.5% and about 4% by weight each with respect to 1,2-dichloropropane.

4. The process of claim 1 wherein the reaction of step (a) is conducted at approximately atmospheric pressure and at a temperature from about 25° C to about 60° C.

5. The process of claim 1 wherein the reaction of step (b) is conducted in the liquid phase and the basic material is selected from the group consisting of aqueous or alcohol solutions of sodium hydroxide, potassium hydroxide, alkaline earth metal hydroxides, and sodium carbonate.

6. The process of claim 1 wherein the reaction of step (b) is conducted in the liquid phase and the basic material is aqueous sodium hydroxide.

7. The process of claim 1 wherein the reaction of step (b) is conducted in the presence of a catalytic amount of a phase transfer catalyst.

8. The process of claim 1 wherein the reaction of step (b) is conducted in the presence of a catalytic amount of benzyltrimethylammonium chloride.

9. The process of claim 1 wherein the reaction of step (b) is conducted at approximately atmospheric pressure and a temperature from about 70° C to about 80° C.

10. The process of claim 1 wherein the amide catalyst of step (c) is dialkyl formamide.

11. The process of claim 1 wherein the amide catalyst of step (c) is dimethyl formamide.

12. The process of claim 1 wherein the amide catalyst added to the reaction mixture of step (c) is from about 0.001 to about 1.0 volume percent with respect to the amount of 1,1-dichloropropene-1 added to the reaction mixture.

13. The process of claim 1 wherein the amide catalyst of step (c) added to the reaction mixture is from about 0.01 to about 0.10 volume percent with respect to the amount of 1,1-dichloropropene-1 added to the reaction mixture.

14. The process of claim 13 wherein the reaction temperature is from about 60° C to about 90° C.

15. The process of claim 13 wherein the reaction temperature is from about 65° C to about 80° C.

16. The process of claim 1 wherein the reaction of step (a) is conducted in the presence of iodine and anydrous aluminum chloride at concentrations between about 0.5% and about 4% by weight each with respect to 1,2-dichloropropane, at approximately atmospheric pressure and at a temperature from about 25° C to about 60° C; the reaction of step (b) is conducted in presence of a catalystic amount of benzyltrimethylammonium chloride at approximately atmospheric pressure and at a temperature from about 70° C to about 80° C; the amide catalyst of step (c) is dimethyl formamide added to the reaction mixture at from about 0.01 to about 0.10 volume percent with respect to the amount of 1,1-dichloropropene-1 added to the reaction mixture; and the reaction temperature of step (c) is from about 65° C to about 80° C.

17. A process for the manufacture of α-chloropropionyl chloride comprising reacting, 1,1-dichloropropene-1 in the liquid phase at a temperature in the range of from about 24° to about 100° C with oxygen in the presence of chlorine or bromine and an activating agent for the chlorine or bromine and further in the presence of a lower alkyl-primary- or -secondary-amide and recovering the produced α-chloropropionyl chloride.

18. The process of claim 17 wherein the amide catalyst is dialkyl formamide.

19. The process of claim 17 wherein the amide catalyst is dimethyl formamide.

20. The process of claim 17 wherein the amide catalyst added to the reaction mixture is from about 0.001 to about 1.0 volume percent with respect to the amount of 1,1-dichloropropene-1 added to the reaction mixture.

21. The process of claim 17 wherein the amide catalyst added to the reaction mixture is from about 0.01 to about 0.10 volume percent with respect to the amount of 1,1-dichloropropene-1 added to the reaction mixture.

22. The process of claim 21 wherein the reaction temperature is from about 60° C to about 90° C.

23. The process of claim 21 wherein the reaction temperature is from about 65° C to about 80° C.

24. The process of claim 17 wherein the amide catalyst is dimethylformamide added to the reaction mixture at from about 0.01 to about 0.10 volume percent with respect to the amount of 1,1-dichloropropene-1 added to the reaction mixture, and the reaction temperature is from about 65° C to about 80° C.

* * * * *